US00PP29990P2

(12) United States Plant Patent
Wood

(10) Patent No.: US PP29,990 P2
(45) Date of Patent: Dec. 18, 2018

(54) ***WEIGELA* PLANT NAMED 'SMNWFRP'**

(50) Latin Name: *Weigela florida*
Varietal Denomination: SMNWFRP

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 15/732,304

(22) Filed: Oct. 20, 2017

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. A. Whealy

(57) ABSTRACT

A new and distinct cultivar of *Weigela* plant named 'SMNWFRP', characterized by its upright and rounded plant habit; freely branching habit; dense and bushy appearance; relatively dark green-colored leaves; freely and remontant flowering habit; light red purple-colored flowers; and good garden performance.

2 Drawing Sheets

Botanical designation: *Weigela florida.*
Cultivar denomination: 'SMNWFRP'.

BACKGROUND OF THE INVENTION

The present invention relates to a new and distinct cultivar of *Weigela* plant, botanically known as *Weigela florida* and hereinafter referred to by the name 'SMNWFRP'.

The new *Weigela* plant is a product of a planned breeding program conducted by the Inventor in Grand Haven, Mich. The objective of the breeding program was to develop new compact and remontant-flowering *Weigela* plants with attractive flower colors.

The new *Weigela* plant is a naturally-occurring whole plant mutation of *Weigela florida* 'Red Prince', not patented. The new *Weigela* plant was discovered and selected by the Inventor as a single flowering plant from within a population of plants of 'Red Prince' in a controlled environment in Grand Haven, Mich. in 2011.

Asexual reproduction of the new *Weigela* plant by softwood stem cuttings since 2011 in Grand Haven, Mich. has shown that the unique features of this new *Weigela* plant are stable and reproduced true to type in successive generations of asexual reproduction.

SUMMARY OF THE INVENTION

Plants of the new *Weigela* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNWFRP'. These characteristics in combination distinguish 'SMNWFRP' as a new and distinct *Weigela* plant:

1. Upright and rounded plant habit.
2. Freely branching habit; dense and bushy appearance.

3. Relatively dark green-colored leaves.
4. Freely and remontant flowering habit.
5. Light red purple-colored flowers.
6. Good garden performance.

In side-by-side comparisons conducted in Grand Haven, Mich., plants of the new *Weigela* differ primarily from plants of the mutation parent, 'Red Prince', in the following characteristics:

1. Plants of the new *Weigela* are more freely flowering than plants of 'Red Prince'.
2. Plants of the new *Weigela* exhibit a remontant flowering habit whereas plants of 'Red Prince' do not exhibit a remontant flowering habit.
3. Plants of the new *Weigela* and 'Red Prince' differ in flower color as plants of 'Red Prince' have red-colored flowers.

Plants of the new *Weigela* can also be compared to plants of the *Weigela hybrida* 'Bokrasopin', disclosed in U.S. Plant Pat. No. 24,572. In side-by-side comparisons plants of the new *Weigela* differ primarily from plants of 'Bokrasopin' in flower color as plants of 'Bokrasopin' have darker red purple-colored flowers.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet is a side perspective view of a typical plant of 'SMNWFRP' grown in an outdoor nursery.

The photograph on the second sheet is a close-up view of a typical flowering plant of 'SMNWFRP'.

DETAILED BOTANICAL DESCRIPTION

Plants used for the aforementioned photographs and the following description were grown during the spring in an outdoor nursery and in one-gallon containers in a polypropylene-covered greenhouse in Grand Haven, Mich. and under cultural practices typical of commercial *Weigela* production. During the production of the plants, day temperatures ranged from 18° C. to 27° C. and night temperatures ranged from 5° C. to 10° C. Plants of the new *Weigela* were two years old when the photographs and description were taken. In the following description, color references are made to The Royal Horticultural Society Colour Chart, 2015 Edition, except where general terms of ordinary dictionary significance are used.

Botanical classification: *Weigela florida* 'SMNWFRP'.

Parentage: Naturally-occurring whole plant mutation of *Weigela florida* 'Red Prince', not patented.

Propagation:

*Type*.—By softwood stem cuttings.

*Time to initiate roots, summer*.—About 15 days at temperatures about 18° C. to 27° C.

*Time to produce a rooted young plant, summer*.—About two months at temperatures about 18° C. to 27° C.

*Root description*.—Fine; fibrous; typically white in color, actual color of the roots is dependent on substrate composition, water quality, fertilizer, substrate temperature and physiological age of roots.

*Rooting habit*.—Freely branching; dense.

Plant description:

*Plant and growth habit*.—Perennial shrub; upright and rounded plant habit; rapid growth rate; vigorous growth habit.

*Branching habit*.—Freely branching habit with about 20 lateral branches developing per plant; pinching enhances lateral branch development; dense and bushy plant form.

*Plant height*.—About 52 cm.

*Plant diameter*.—About 44 cm.

Lateral branch description:

*Length*.—About 27 cm.

*Diameter*.—About 4 mm.

*Internode length*.—About 7 cm to 8 cm.

*Texture*.—Pubescent.

*Strength*.—Strong.

*Aspect*.—Mostly upright.

*Color*.—Close to N144C.

Leaf description:

*Arrangement*.—Opposite; simple.

*Length*.—About 6.2 cm.

*Width*.—About 3.3 cm.

*Shape*.—Ovate to oblanceolate.

*Apex*.—Acute.

*Base*.—Rounded.

*Margin*.—Serrulate.

*Texture, upper surface*.—Slightly pubescent; leathery.

*Texture, lower surface*.—Pubescent; rough with prominent venation.

*Venation pattern*.—Pinnate.

*Color*.—Developing leaves, upper surface: Close to 143A. Developing leaves, lower surface: Close to 143C. Fully expanded leaves, upper surface: Close to 137A; venation, close to 145A. Fully expanded leaves, lower surface: Close to 143C; venation, close to 145C.

*Petioles*.—Length: About 3.5 mm. Diameter: About 2 mm. Texture, upper and lower surfaces: Pubescent. Color, upper surface: Close to 145A. Color, lower surface: Close to 145C.

Flower description:

*Flower arrangement and habit*.—Salverform flowers arranged in terminal clusters of four to seven flower each; flowers face mostly outwardly to downwardly.

*Fragrance*.—Slightly fragrant; sweet, pleasant.

*Natural flowering season*.—Plants of the new *Weigela* exhibit a remontant flowering habit during the spring in Grand Haven, Mich.; flowers not persistent.

*Flower cluster diameter*.—About 9 cm.

*Flower cluster height*.—About 7 cm to 10 cm.

*Flower diameter*.—About 3.1 cm.

*Flower length* (*height*).—About 4.2 cm.

*Flower throat diameter*.—About 1.2 cm.

*Flower tube length*.—About 2.9 cm.

*Flower tube diameter, proximally*.—About 3 mm.

*Flower buds*.—Length: About 3 cm. Diameter: About 1.1 cm. Shape: Obovate to spatulate. Color: Close to 71B; towards the base, close to 65B.

*Corolla*.—Arrangement: Salverform; five petals fused into a tube with separate petal lobes. Petal lobe length: About 1.1 cm. Petal lobe width: About 1.2 cm. Petal lobe shape: Roughly obovate to oblanceolate. Petal lobe apex: Obtuse. Petal lobe margin: Entire; slightly undulate. Petal texture, upper and lower surfaces: Smooth, glabrous. Throat texture: Smooth, glabrous. Tube texture: Slightly creased, glabrous. Color: When opening, upper surface: Close to 75B. When opening, lower surface: Close to 75B and 64B. Fully opened, upper surface: Close to 75A; color does not fade with development. Fully opened, lower surface: Close to 75B and NN74C. Throat: Close to 75A and 6A. Tube: Close to NN74C.

*Sepals*.—Quantity per flower: Five in a single whorl, fused; campanulate calyx. Length: About 7 mm. Width: Less than 1 mm. Shape: Narrowly triangular, elongated. Apex: Acute. Margin: Entire. Sepal texture, upper and lower surfaces: Smooth; glabrous; coriaceous. Color, upper surface: Close to NN144A. Color, lower surface: Close to NN144C.

*Peduncles*.—Length: About 2.3 cm. Diameter: About 1.5 mm. Strength: Strong; flexible. Aspect: Upright to outwardly. Texture: Slightly pubescent; coriaceous. Color: Close to 166B.

*Reproductive organs*.—Stamens: Quantity and arrangement: Five per flower. Filament length: About 2.1 cm. Filament color: Close to 73A. Anther shape: Narrowly oblong. Anther size: About 8 mm. Anther color: Close to 155B. Pollen amount: Moderate. Pollen color: Close to 155B. Pistils: Quantity: One per flower. Pistil length: About 3.1 cm. Style length: About 3 cm. Style color: Close to 155B. Stigma shape: Flattened globular. Stigma color: Close to 155B. Seeds and fruits: Seed and fruit development has not been observed on plants of the new *Weigela* to date.

Garden performance: Plants of the new *Weigela* have exhibited good tolerance to rain, wind and have been observed to tolerate temperatures from about −32° C. to about 36° C.

Pathogen & pest resistance: To date, plants of the new *Weigela* have not been observed to be resistant to pathogens and pests common to *Weigela* plants.

It is claimed:

1. A new and distinct *Weigela* plant named 'SMNWFRP' as illustrated and described.

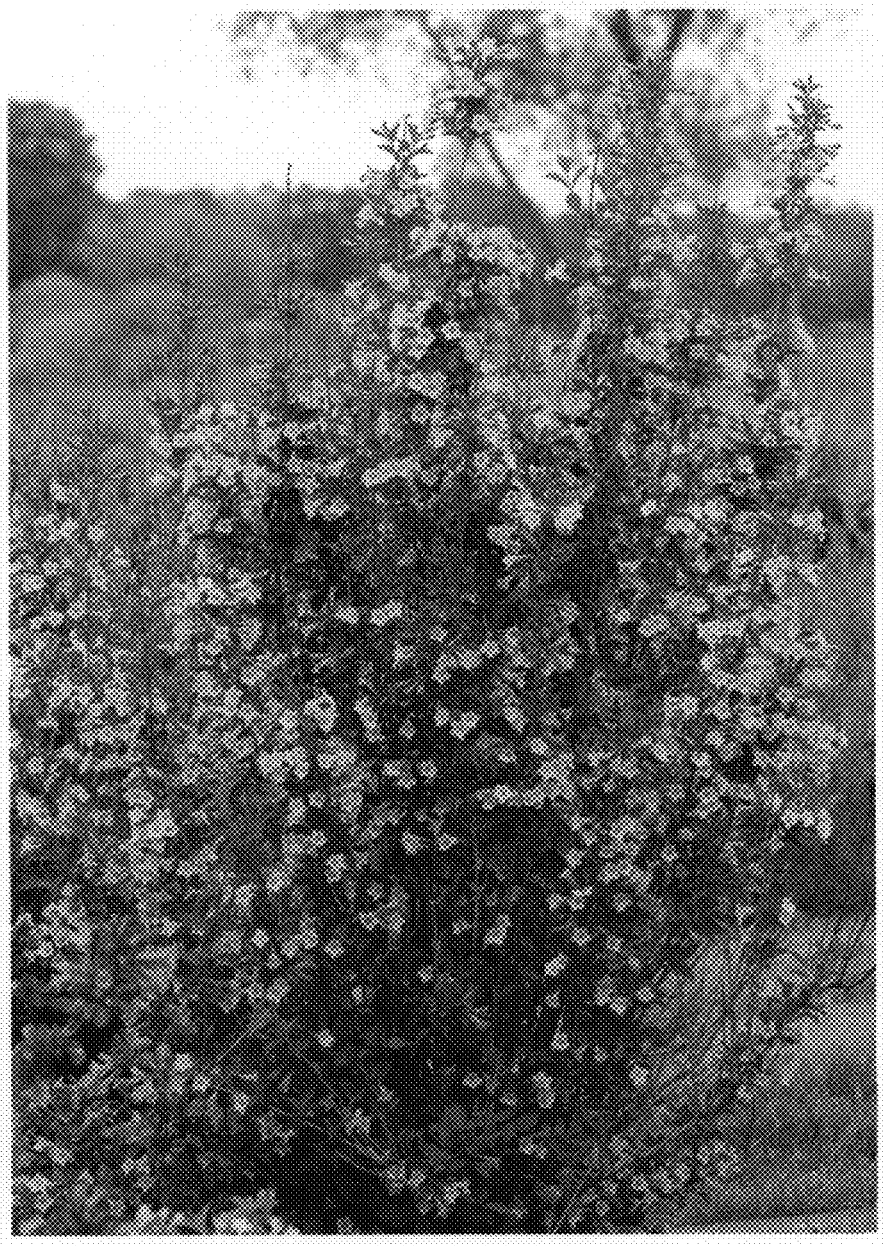

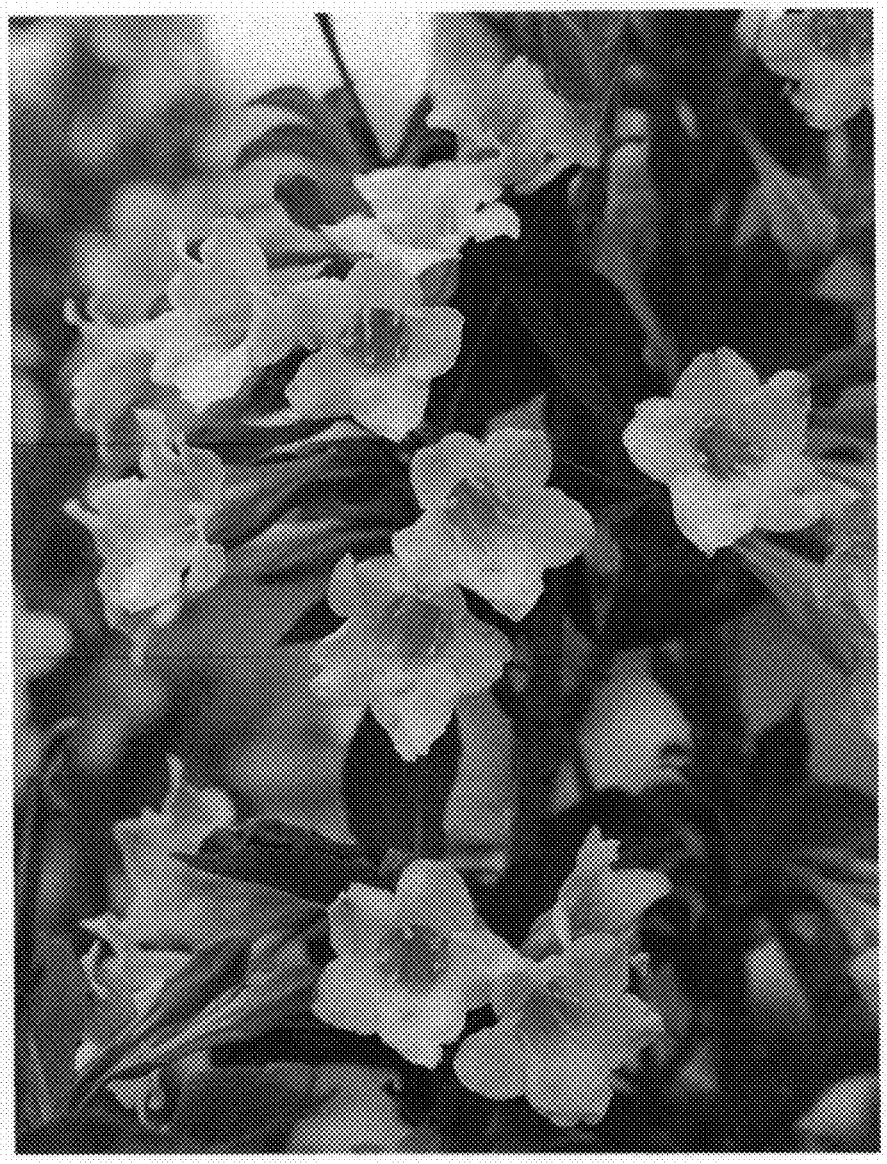

* * * * *